United States Patent [19]

Fikentscher et al.

[11] Patent Number: 5,036,699
[45] Date of Patent: Aug. 6, 1991

[54] APPARATUS FOR TESTING FUEL ADDITIVES AND OIL ADDITIVES

[75] Inventors: Rolf Fikentscher; Knut Oppenlaender, both of Ludwigshafen; Roland Schwen, Friedelsheim, all of Fed. Rep. of Germany

[73] Assignee: BASF Aktiengesellschaft, Ludwigshafen, Fed. Rep. of Germany

[21] Appl. No.: 422,455

[22] Filed: Oct. 17, 1989

[30] Foreign Application Priority Data

Nov. 4, 1988 [DE] Fed. Rep. of Germany ....... 3837470

[51] Int. Cl.$^5$ .................... G01N 5/00; G01N 11/00
[52] U.S. Cl. ..................... 73/61.2; 73/61.3; 73/64; 73/61.1 R; 436/25; 436/29; 436/60; 436/157; 422/68.1; 422/78
[58] Field of Search ............... 436/25, 29, 60, 157, 436/; 422/78, 68.1; 73/61.2, 61.3, 61.1 R, 64

[56] References Cited

U.S. PATENT DOCUMENTS

| | | | |
|---|---|---|---|
| 3,059,467 | 10/1962 | Meguerian | 73/61.2 |
| 3,108,468 | 10/1963 | Mickel | 73/61.2 |
| 3,200,638 | 8/1965 | DeHaut | 73/64 |
| 3,224,838 | 12/1965 | Evans et al. | 422/93 |

FOREIGN PATENT DOCUMENTS

| 888622 | 9/1953 | Fed. Rep. of Germany | 421/703 |
|---|---|---|---|
| 968645 | 9/1964 | United Kingdom . | |

OTHER PUBLICATIONS

Deneshgari et al., *Motortechnische Zeitschrift* 49, 397–402 (1988).

Primary Examiner—David L. Lacey
Assistant Examiner—David Redding
Attorney, Agent, or Firm—Keil & Weinkauf

[57] ABSTRACT

A sample of a fuel/oil/additive mixture is metered continuously to a channel-like, inclined test element along which there is an increasing temperature profile. Under the increasing action of heat on the flowing mixture, solid residual products form on the test element after a certain flow distance. Their weight and the flow distance are evaluated in order to evaluate the additive.

1 Claim, 1 Drawing Sheet

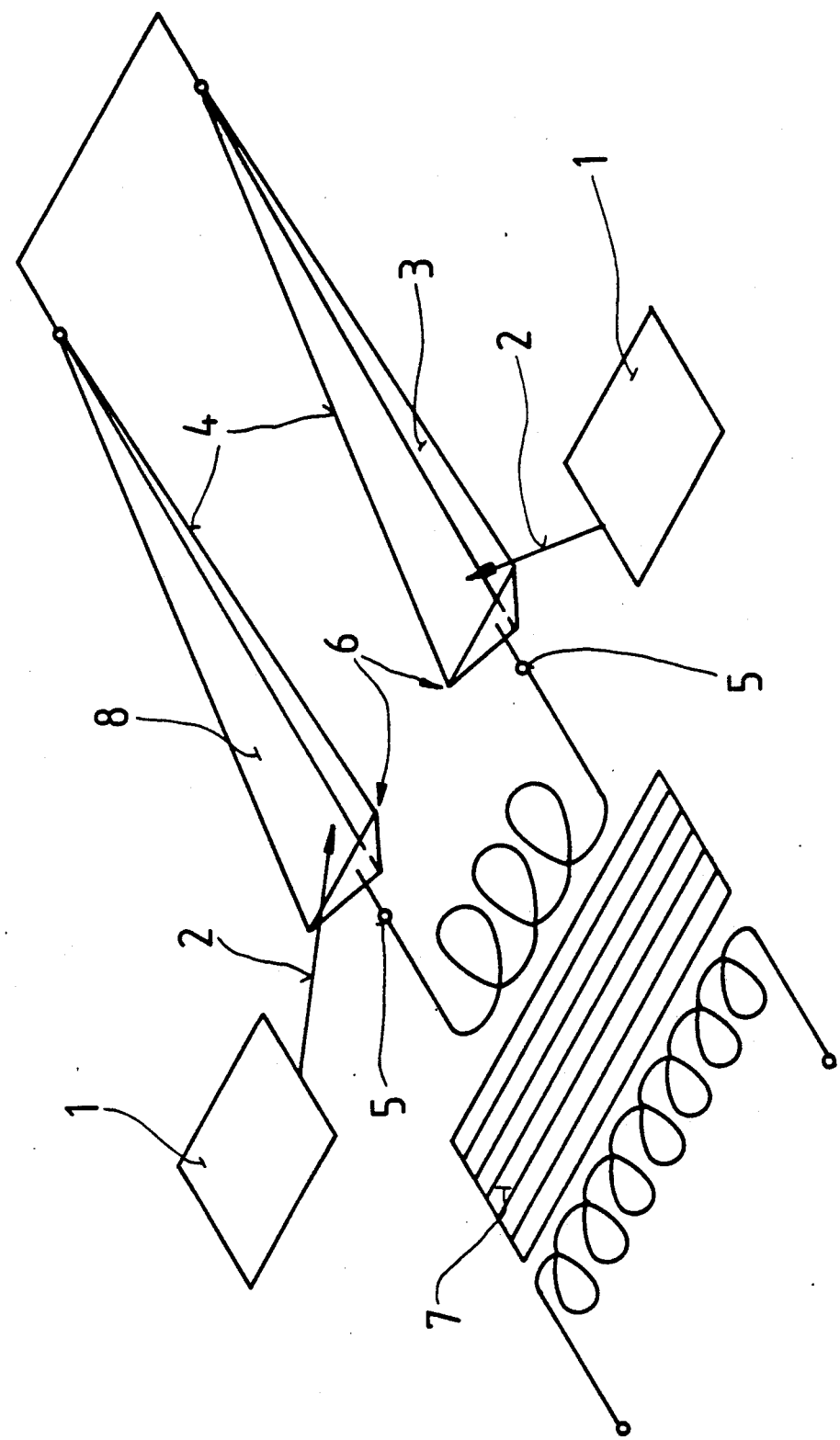

APPARATUS FOR TESTING FUEL ADDITIVES AND OIL ADDITIVES

The present invention relates to a method for testing fuel additives and oil additives for internal combustion engines and to an apparatus for carrying out the method.

In gasoline engines, there is a danger of soiling [M. Völtz, Erdöl und Kohle-Erdgas-Petrochemie, 40 (1987), 270], in particular of the intake system [Automotive Engineering 96 (April 1988), 68] and of the intake valve disk [Automotive Engineering 95 (November 1987), 69], in the form of tar-like deposits and carbon.

Similar damage has been reported by the market and can be reproduced in engine test-bed tests and in car fleet tests. However, there are the following disadvantages:

The engine tests and, to an even greater extent, the car fleet tests are expensive and time-consuming.

Reproducibility is obtained or is possible only at great expense, because the effect of, for example, the fuel grade, i.e. the individual fuel batch, cannot be taken into acount and the mutual effect of fuel, including its additives, and lubricating oil requires a large number of test combinations.

It is an object of the present invention to provide a method and apparatus for testing fuel additives and oil additives, the said method and apparatus meeting the following test conditions:

Duration of action of the fuel/oil/additive mixture

Temperature profile: at intake valves of modern gasoline engines, temperatures from ambient temperatures to about 400° C. are measured, depending on the operating state.

Metallic surface in contact with the mixture

Fuel grade or fuel batch

Fuel additives

Oil and additives (in the fresh state or aged)

We have found that this object is achieved by a method in which a sample of a fuel/oil/additive mixture is metered continuously to a treatment zone in which the temperature increases along the flow path of the sample of the mixture, in accordance with engine operation, and the resulting solid residual products are evaluated according to weight and flow distance to the point at which the residue has formed, in order to evaluate the additives.

BRIEF DESCRIPTION OF DRAWING

The drawing illustrates one possible arrangement of the apparatus

The apparatus by means of which the object is achieved consists of an inclined, channel-like metal test element having a heating means for producing an increasing temperature profile along the element, a metering means having a feed for the sample of mixture being coordinated with that end of the test element which is at the lower initial temperature.

The invention is described in detail below with reference to an embodiment shown schematically in the drawing.

A sample of the fuel/oil/additive mixture to be tested is introduced by means of a metering pump 1 via a feed 2 onto a channel-like metal test element 3 sloping downward at an angle of about 10 degrees. On the test element, the sample of mixture flows slowly toward the other end and should be exposed to increasing temperatures which are in a range corresponding to the engine operation.

For this purpose, the test element is equipped with a heating means 4 which keeps the element at a temperature profile which increases starting from the feed end, for example from 200° C. up to 400° C. The heating means may be, for example, in the form of a heat exchanger, so that the test element is surrounded by a heating medium. Another possibility consists in electrical heating, for example by inductive energy transfer or by resistance heating. The latter is advantageously used in the present embodiment, in which the test element 3 is connected at both its ends to a voltage source 5, and the cross-sectional area of the element decreases continuously starting from the feed end 6 in order to achieve increasing electrical resistance and hence the production of an ascending temperature profile. The cross-sectional change can be obtained by means of decreasing material thickness or decreasing element width or by both. Since readily ignitable materials are heated, a low voltage supply provided by a suitable transformer 7 is advisable.

It is advantageous to provide a preheating time dependent on the nature of the test element, for example one hour, in order to ensure a stable temperature profile. The surface temperatures can be measured, for example, with the aid of thermocouples or surface thermometers or thermocolors.

To carry out several measurements simultaneously, a plurality of test elements can be connected together, identical material, identical material thickness and identical contours guaranteeing a standard temperature profile when the test elements are connected in series.

Regarding metering of the mixture, it is assumed that a typical four-cycle gasoline engine, in which the intake valves tend to become soiled, has an oil loss of 1 g/h per valve stem guide and consumes 2 liters of fuel per hour per cylinder. If it were desired to evaporate this amount of fuel on a heated test element, the element would be excessively cooled by this fuel in the starting area and there would be a considerable danger of explosion. Hence, for example, 90% of the 2 liters of fuel are distilled off via a laboratory column and the residue of 10% is used for the measurement. The critical amount of oil of the quality to be tested, i.e. 1 g, and the fuel additive to be tested, e.g. 1,000 ppm, are added to the said residue. The mixture is then introduced onto the test element continuously in the course of one hour.

When the mixture is subjected to heat, solid residues of tar-like products and carbon form on the test element after a certain flow distance. Their weight and the flow distance are recorded for evaluation of the additives.

A long flow distance and/or low residue weight indicate an effective additive.

In engine operation, liquid fuel reaches the intake valve during a cold start. To simulate their washing effect, the test elements with the residues are then washed with gasoline at about 50° C., for example for 2 minutes, and the remaining residues are weighed again. In this case, too, low values indicate a good result.

In a particularly advantageous test arrangement, a second, identical test element 8 is provided for a parallel reference measurement of a fuel/oil mixture without additives. The two test elements 3 and 8 are connected in series to the voltage source 5 in order to obtain corresponding temperature profiles. The test process is as described above, the efficiency of the additive to be tested being determined in a simple manner from the difference between the residue weights and the flow distances of the two measurements.

To illustrate the novel additive test, a measurement which has been carried out is described below.

EXAMPLE

Fuel: premium grade gasoline
Oil: multigrade engine oil RL 51
1,000 ppm of additive or without additive The test element consists of steel St 37 and is 46 cm long without the power connections; its crosssectional area is 55 mm$^2$ at the beginning and 35 mm$^2$ at the end. After the heating-up period, the voltage for heating the test element is 1.4 V and the current consumption is 260 A. The temperature of the test element is from 200° C. at the feed end to 450° C. at the outflow end. The test element is inclined 10° with respect to the horizontal.

| | Test result: | | |
|---|---|---|---|
| | | Weight of residue [g] | |
| | Flow distance [cm] | before washing | after washing |
| Reference measurement | 23 | 0.31 | 0.23 |
| Measurement with additive A | 30.5 | 0.24 | 0.14 |
| Measurement with additive B | 25 | 0.57 | 0.40 |

This shows that additive A and additive B are effective since they have longer flow distances than the flow distance in the reference measurement, and additive A is better than additive B because it has a longer flow distance as well as the smallest amount of residue, both before and after washing.

We claim:

1. In an apparatus for testing fuel additives and oil additives for internal combustion engines, comprising an metal test element constructed so as to form an incline having a cross-sectional area and having a means for producing an increasing temperature profile along the element, a metering means having a feed for the sample of mixture being coordinated with that end of the test element which is at the lower initial temperature, the improvement comprising (1) electrical connections attached to each end of the metal test element to provide direct heating of the element and (2) the cross-sectional area of the metal test element decreases continuously starting from one end to its other end so as to achieve increasing electrical resistance and the corresponding increasing temperature profile.

* * * * *